United States Patent
Banerjee et al.

(10) Patent No.: US 9,861,653 B2
(45) Date of Patent: Jan. 9, 2018

(54) SYNERGISTIC ANTI-CANCER COMPOSITION AND A PROCESS FOR THE PREPARATION THEREOF

(71) Applicants: Council of Scientific and Industrial Research, New Delhi (IN); Mayo Foundation for Medical Education and Research, Rochester, MN (US)

(72) Inventors: Rajkumar Banerjee, Hyderabad (IN); Debabrata Mukhopadhyay, Rochester, MN (US)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/427,814

(22) PCT Filed: Sep. 12, 2013

(86) PCT No.: PCT/IN2013/000552
§ 371 (c)(1),
(2) Date: Mar. 12, 2015

(87) PCT Pub. No.: WO2014/041563
PCT Pub. Date: Mar. 20, 2014

(65) Prior Publication Data
US 2015/0283166 A1    Oct. 8, 2015

(30) Foreign Application Priority Data

Sep. 12, 2012 (IN) .......................... 2849/DEL/2012

(51) Int. Cl.

| | | |
|---|---|---|
| *A61K 9/127* | (2006.01) | |
| *A61K 31/496* | (2006.01) | |
| *A61K 31/4439* | (2006.01) | |
| *A61K 31/575* | (2006.01) | |
| *A61K 48/00* | (2006.01) | |
| *B82Y 5/00* | (2011.01) | |
| *A61K 31/7105* | (2006.01) | |
| *A61K 31/573* | (2006.01) | |
| *A61K 31/567* | (2006.01) | |
| *A61K 45/06* | (2006.01) | |
| *A61K 9/00* | (2006.01) | |
| *C12N 15/113* | (2010.01) | |

(52) U.S. Cl.
CPC ........ *A61K 31/7105* (2013.01); *A61K 9/0019* (2013.01); *A61K 9/127* (2013.01); *A61K 31/496* (2013.01); *A61K 31/567* (2013.01); *A61K 31/573* (2013.01); *A61K 31/575* (2013.01); *A61K 45/06* (2013.01); *C12N 15/1138* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | |
|---|---|---|
| 6,333,433 B1 | 12/2001 | Banerjee et al. |
| 6,346,516 B1 | 2/2002 | Banerjee et al. |
| 6,503,945 B2 | 1/2003 | Banerjee et al. |
| 6,541,649 B2 | 4/2003 | Banerjee et al. |
| 8,012,952 B2 | 9/2011 | Bathula et al. |

FOREIGN PATENT DOCUMENTS

| | | |
|---|---|---|
| WO | WO-2008/026223 | 3/2008 |
| WO | WO-2008/099414 | 8/2008 |
| WO | WO-2014/041563 | 3/2014 |

OTHER PUBLICATIONS

Ganjavi et al., Adenovirus-mediated p53 gene therapy in osteosarcoma cell lines: sensitization to cisplatin and doxorubicin. Cancer Gene Therapy (2006) 13, 415-419.*
Vassilev et al., In Vivo Activation of the p53 Pathway by Small-Molecule Antagonists of MDM2. Science (2004) 303:844-848.*
Wang et al., Neuropilin-1 Modulates p53/Caspases Axis to Promote Endothelial Cell Survival. PLoS One, 2007, 11(e1161):1-14.*
Wang et al., Silencing Livin gene expression to inhibit proliferation and enhance chemosensitivity in tumor cells. Cancer Gene Therapy (2008) 15, 402-412.*
Kalra et al., Development of 5-FU and Doxorubicin-Loaded Cationic Liposomes against Human Pancreatic Cancer: Implications for Tumor Vascular Targeting. Pharmaceutical Research, vol. 23, No. 12, Dec. 2006, pp. 2809-2817.*

(Continued)

*Primary Examiner* — Scott Long
*Assistant Examiner* — Arthur S Leonard
(74) *Attorney, Agent, or Firm* — Schwegman Lundberg & Woessner, P.A.

(57) ABSTRACT

The present invention provides an anti-cancer lipid-based composition that kills very aggressive pancreatic cancer cells and breast cancer stem cell (CSC)-like cells. This composition is a concoction of an anti-cancer agent, ESC8 and a glucocorticoid receptor (GR)-targeting cationic lipid delivery system, DX which is further complexed with plasmid DNA. This composition shows anti-cancer effect and initiates killing of cancer cells and CSC-like cells within 3 h. When anti-cancer gene encoded plasmid is used, residual cancer cells were also significantly eradicated after 2 days of exposure. The formulation-free naked ESC8 requires at least ten-fold more concentration and 3 days of continuous treatment to get a similar level of killing. The composition could also inhibit the tumor growth in mice orthotopically implanted with very aggressive mouse breast cancer cell, ANV-1. This cell is known to produce breast CSC-like cells that show phenotype of advanced cancer relapsing. There is no visible toxic effect of this composition when injected in mice, indicating that it has minimum to no toxic effect to normal homeostasis. The present invention is likely to find specific application in developing potential therapeutic treatment for aggressive cancers and CSC-like cancers.

13 Claims, 6 Drawing Sheets

(56) References Cited

OTHER PUBLICATIONS

Nielsen et al., Adenovirus-mediated p53 gene therapy and paclitaxel have synergistic efficacy in models of human head and neck, ovarian, prostate, and breast cancer. Clin Cancer Res. Apr. 1998;4(4):835-46.*
Graat et al., Enhanced tumor cell kill by combined treatment with a small-molecule antagonist of mouse double minute 2 and adenoviruses encoding p53. Mol Cancer Ther 2007;6(5):1552-61.*
"International Application No. PCT/IN2013/000552, International Preliminary Report on Patentability dated Mar. 17, 2015", 5 pgs.
"International Application No. PCT/IN2013/000552, Written Opinion dated Feb. 19, 2014", 4 pgs.
Banerjee, Rajkumar, et al., "Novel Series of Non-Glycerol-Based Cationic Transfection Lipids for Use in Liposomal Gene Delivery", *J. Med. Chem.*, 42. (1999), 4292-4299.
Cao, Ying, et al., "Neuropilin-1 Upholds Dedifferentiation and Propagation Phenotypes of Renal Cell Carcinoma Cells by Activating Akt and Sonic Hedgehog Axes", *Cancer Research*, 68(21), (2008), 8667-8672.
Cole, Timothy J., et al., "Targeted disruption of the glucocorticoid receptor gene blocks adrenergic chromaffin cell development and severly retards lung maturation", *Genes & Development*, 9, (1995), 1608-1621.
Corroyer, Sophie, et al., "Involvement of the Cell Cycle Inhibitor CIP1/WAF1 in Lung Alveolar Epithelial Cell Growth Arrest Induced by Glucocorticoids", *Endocrinology*, 138(9), (1997), 3677-3685.
Goya, Luis, et al., "Glucocorticoids Induce a G1/G0 Cell Cycle Arrest of Con8 Rat Mammary Tumor Cells That Is Synchronously Reversed by Steroid Withdrawal or Addiction of Transforming Growth Factor-α", *Molecular Endocrinology*, 7(9), (1993), 1121-1132.
Gray, Michael J., et al., "Neuropilin-1 Suppresses Tumorigenic Properties in a Human Pancreatic Adenocarcinoma Cell Line Lacking Neuropilin-1 Coreceptors", *Cancer Research*, 65(9), (2005), 3664-3670.
Greenberg, Alissa K., et al., "Glucocorticoids Inhibit Lung Cancer Cell Growth through Both the Extracellular Signal-Related Kinase Pathway and Cell Cycle Regulators", *Am. J. Respir. Cell Mol. Biol.*, 27, (2002), 320-328.
Gruneich, J. A., et al., "Cationic corticosteroid for nonviral gene delivery", *Gene Therapy*, 11, (2004), 668-674.
Hong, Tse-Ming, et al., "Targeting Neuropilin 1 as an Antitumor Strategy in Lung Cancer", *Clin. Cancer Res.*, 13(16), (2007), 4759-4768.
Lapidot, Tsvee, et al., "A cell initiating human acute myeloid leukaemia after transplantation into SCID mice", *Nature*, 367, (1994), 645-648.
Leonard, Martin O., et al., "Potentiation of Glucocorticoid Activity in Hypoxia through Induction of the Glucocorticoid Receptor", *Journal of Immunology*, 174(4), (2005), 2250-2257.
Li, Ruo-Jing, et al., "All-trans retinoic acid stealth liposomes prevent the relapse of breast cancer arising from the cancer stem cells", *Journal of Controlled Release*, 149, (2011), 281-291.
Lukaszewicz, Agnes I., et al., "Perspective: Small Molecules and Stem Cells' Potency and Lineage Commitment: The New Quest for the Fountain of Youth", *NIH Public Access*, Author Manuscript, available in PMC May 13, 2011, published in final edited form as: J. Med. Chem., 53(9), (2010), 3439-3453, (2011), 27 pgs.
Mukherjee, Amarnath, et al., "Selective Cancer Targeting via Aberrant Behavior of Cancer Cell-associated Glucocorticoid Receptor", *Molecular Therapy*, 17(4), (2009), 623-631.
Pore, Subrata K., et al., "Hsp90-targeted miRNA-liposomal formulation for systemic antitumor effect", *Biomaterials*, 34(28), (2013), 6804-6817.
Ramalingam, Arivudainambi, et al., "Glucocorticoid Inhibition of Fibroblast Proliferation and Regulation of the Cyclin Kinase Inhibitor p21$^{Cip1}$", *Molecular Endocrinology*, 11(5), (1997), 577-586.
Rider, Lisa G., "Activation of the Mitogen-Activated Protein Kinase Cascade Is Suppressed by Low Concentrations of Dexamethasone in Mast Cells", *The Journal of Immunology*, 157, (1996), 2374-2380.
Rogatsky, Inez, et al., "Glucocorticoid Receptor-Mediated Cell Cycle Arrest Is Achieved through Distinct Cell-Specific Transcriptional Regulatory Mechanisms", *Molecular and Cell Biology*, 17(6), (1997), 3181-3193.
Santisteban, Marta, et al., "Immune-Induced Epithelial to Mesenchymal Transitition In vivo Generates Breast Cancer Stem Cells", *Cancer Research*, 69(7), (2009), 2887-2895.
Singh, Rajkumar S., et al., "Anchor Dependency for Non-Glycerol Based Cationic Lipofectins: Mixed Bag of Regular and Anomalous Transfection Profiles", *Chem. Eur. J.*, 8(4), (2002), 900-909.
Sinha, Sutapa, et al., "A Lipid-Modified Estrogen Derivative that Treats Breast Cancer Independent of Estrogen Receptor Expression through Simultaneous Induction of Autophagy and Apoptosis", *Mol. Cancer Res.*, 9, (2011), 364-374.
Wang, Ling, et al., "Neuropilin-1-mediated vascular permeability factor/vascular endothelial growth factor-dependent endothelial cell migration", *J. Biol. Chem.*, 278(49), (2003), 48848-48860.
Wattenberg, Lee W., et al., "Chemopreventive Effects of myo-Inositol and Dexamethasone on Benzo[a]pyrene and 4-(Methylnitrosoamino)-1-(3-pyridyl)-1-butanone-induced Pulmonary Carcinogenesis in Female A/J Mice", *Cancer Research*, 56(22), (1996), 5132-5135.
Wey, J. S., et al., "Overexpression of neuropilin-1 promotes constitutive MAPK signalling and chemoresistance in pancreatic cancer cells", *Br. J. Cancer*, 93, (2005), 233-241.
Yamamoto, Keith R., "Steroid receptor regulated transcription of specific genes and gene networks". *Annu Rev Genet*, vol. 19, (1985), 209-252.
Zhang, Jingying, et al., "Targeting of the B-lineage leukemia stem cells and their progeny with norcantharidin encapsulated liposomes modified with a novel CD19 monoclonal antibody 2E8 in vitro", *Journal of Drug Targeting*, 18(9), (2010), 675-687.
"International Application No. PCT/IN2013/000552, International Search Report dated Feb. 19, 2014", (dated Feb. 19, 2014), 3 pgs.
Kunstfeld, Rainer, et al., "Paclitaxel Encapsulated in Cationic Liposomes Diminishes Tumor Angiogenesis and Melanoma Growth in a "Humanized" SCID Mouse Model", J Invest Dermatol 120(3):476-482, 2003, (Mar. 2003), 476-482.
Lee, Chun Man, et al., "Novel Chondroitin Sulfate-binding Cationic Liposomes Loaded with Cisplatin Efficiently Suppress the Local Growth and Liver Metastasis of Tumor Cells in Vivo", Cancer Research 62, 4282-4288, Aug. 1, 2002, (Aug. 1, 2002), 4282-4288.

* cited by examiner

SEQUENCE LISTING

<160> NUMBER OF SEQ ID NOS: 1

<210> SEQ ID NO 1
<211> LENGTH: 21
<212> TYPE: DNA
<213> ORGANISM: Mus musculus

<400> SEQUENCE: 1
ccagagaatc ataatcaact t                                              21

SYNERGISTIC ANTI-CANCER COMPOSITION AND A PROCESS FOR THE PREPARATION THEREOF

PRIORITY CLAIM TO RELATED APPLICATIONS

This application is a U.S. national stage application filed under 35 U.S.C. § 371 from International Application Serial No. PCT/IN2013/000552, which was filed Sep. 12, 2013, and published as WO 2014/041563 on Mar. 20, 2014, and which claims priority to India Application No. 2849/DEL/2012, filed Sep. 12, 2012, which applications and publication are incorporated by reference as if reproduced herein and made a part hereof in their entirety, and the benefit of priority of each of which is claimed herein.

TECHNICAL FIELD OF THE INVENTION

The present invention relates to a synergistic anti-cancer composition for simultaneous gene therapy and drug delivery for cancer treatment and a process for the preparation thereof. More particularly, the present invention relates to the enhanced non-viral delivery of genetic products and drug molecules simultaneously to cancer cells utilizing expressed glucocorticoid receptors.

BACKGROUND AND PRIOR ART OF THE INVENTION

Small molecule-based chemotherapy and radiation therapies are two important clinical modalities for treatment of cancer. These therapies are often plagued with non-specific toxicity and collateral damage to vital organs and nearby non-cancerous tissues even though they show high efficiency towards solid tumor-regression. The modalities seemingly cease to work during the relapsing of disease possibly because of incomplete cell killing or residual cells acquiring drug resistance leading to the evolution of cancer stem cell (CSC)-like behavior. These drug resistant cells are differentiated into highly aggressive cancer cells and often metastasize shortly into vital organs leading to enhanced mortality.

Glucocorticoid receptor (GR) is a nuclear hormone receptor residing ubiquitously in almost all cells including most cancer cells because of its vital role in gluconeogenesis. This receptor in a ligand-bound state acts as a transcription factor in nucleus through binding to glucocorticoid response elements (GRE) in the promoter sequences of various GR responsive genes and regulates their transcription.

Dexamethasone (dex), a synthetic glucocorticoid (GR hormone-like molecule) exhibits antiproliferative effect on several tissues of different origin (Corroyer, S. E. et al. 1997, *Endocrinology*, 138, 3677-3685; Ramalingam, A. et al. 1997, *Mol. Endocrinology*, 11, 577-586; Rider, L. G. et al. 1996, *J. Immunol.*, 157, 2374-2380; Goya, L. et al. 1993, *Mol. Endocrinology*, 7, 1121-1132; Wattenberg, L. W., and Estensen, R. D. 1996, *Cancer Res.*, 56, 5132-5135; Greenberg A. K. et al. 2002, *Am. J. Respir. Cell Mol. Biol.*, 27, 320-328) as well as regulates and controls metabolism, development, inflammation, cell growth, proliferation and differentiation (Yamamoto K. R. 1985, *Annu. Rev. Genet.* 19, 209-252; Cole, T. J. et al. 1995, *Genes Dev.*, 9, 1608-1621; Rogatsky, I. et al. 1997, *Mol. Cell Biol.*, 17, 3181-3193). GR-mediated glucocorticoid-signaling potentiates a possible hypoxia related pathway leading to inflammation. As an anti-inflammatory agent, dex inhibits hypoxia inducible factor (HIF-1), which has direct role in mediating angiogenesis through up-regulation of VEGF (Leonard, M. W. et al. 2005, *J. Immunol.*, 174, 2250-2257). Hence, dexamethasone (dex) is a very important and inexpensive drug-like substitute used in various pathological conditions. As a gene carrier agent, dex-spermine conjugate was used to deliver genes to airway epithelial with concurrent reduction of inflammation (Gruneich J. A. 2004, *Gene Ther*, 11, 668-674).

The viral based gene delivery is extensively used for their phenomenally efficient process of delivering genes to wide variety of cells. However, a number of problems including host toxicity, immunogenic responses and non-specific genomic integration of transferred gene make viral delivery a risky option for delivering genes. In comparison, non-viral gene delivery is a much more robust and clinically safe option compared to viral counterparts.

Banerjee, R. et al. U.S. Pat. Nos. 6,346,516 B1; 6,333,433 B1; 6503945 and 6541649; Banerjee, R. et al. 1999, *J. Med. Chem.*, 42, 4292-4299, Singh R S et al. 2002, *Chem Eur J.*, 8, 900-909 disclose, DODEAC (N,N-dihydroxyethyl, N,N-dioctadecyl ammonium chloride) and its generic structures, which forms cationic liposome using co-lipid cholesterol in membrane filtered water. Mukherjee, A. and Banerjee, R. Indian Application No. 1936/DEL/2006 and PCT/IN2007/000367, EP-2061514-A2 and Mukherjee, A. et al. 2009, *Mol Ther.*, 17, 623-631 illustrate that upon associating dex with 'DODEAC: cholesterol' to formulate DODEAC: cholesterol: dex (called DX hereafter), cancer cells can be efficiently and GR-specifically targeted for the delivery of reporter and anticancer genes. It has also been shown that DX simultaneously translocates genetic and lipid cargo inside the cancer cell-nuclei.

Recently, a potent anti-cancer estrogen-structure-based drug, ESC8 (17-α-[3-(N,N-dioctyl,N-methyl-amino)-propan-1-yl]-17β-estradiol) has been developed anticipating similar observation in another nuclear hormone receptor, estrogen receptor (ER) in breast cancer cells. ESC8 kills human breast cancer cells with high selectivity irrespective of its estrogen receptor (ER)-expression status (Reddy, B. S., and Banerjee, R. Indian patent Application No. 0278/DEL/2007 and PCT Application No.; PCT/IN-07/00615; Sinha, S. et al. 2011, *Mol. Cancer Res.*, 9, 364-374; U.S. Pat. No. 8,012,952).

Furthermore, it is known that Neuropilin (NRP-1) is a membrane protein highly expressed in several cell types, including many cancer cells. Expression of NRP-1 in tumor correlates with advanced tumor stage and poor prognosis in some specific tumor types. MAPK (Gray, M. J., et al. 2005, *Cancer Res.*, 65, 3664-3670; Wey, J. S., et al. 2005, *Br. J. Cancer.*, 93, 233-241), PI3K/Akt (Hong, T. M., et al. 2007, *Clin. Cancer Res.*, 13, 4759-4768; Wang, L., et al. 2003, *J. Biol. Chem.*, 278, 48848-48860) and Rho/Rac (Cao, Y., et al. 2008, *Cancer Res.*, 68, 8667-8672; Wang, L., et al. 2003, *J. Biol. Chem.*, 278, 48848-48860) signaling were found to be regulated by NRP-1 and to control cell migration, invasion, and apoptosis.

The observation that cancer cells have a self-renewal mechanism similar to that of stem cells raised the concept of cancer stem cells (CSC). Only a few CSCs from tumor populations result in tumor in the animal model. Lapidot's observation in 1994 that leukemia can be reconstituted in SCID mice with a single leukemia-initiating cell that had an immature (i.e. stem-like) phenotype has raised speculation that cancers are driven by a CSC (Lapidot, T. et al. 1994, *Nature* 367, 645-648). CSCs provide a useful insight for research into the effective treatment of cancer particularly in advanced, aggressive and relapsing phenotype of cancer. The ANV-1 cell line, the breast CSC-like cell with mesenchymal characters, was raised by immunoediting breast tumors in a neu-transgenic (neu-tg) mouse. The cells went through an epithelial-to-mesenchymal transition (EMT) and acquired the breast CSC character (Santisben et al. 2009, *Cancer Res.*, 69, 2887-2895). It is a good model for the investigation of NRP-1 in CSCs. It has been found that ANV-1 cells express fourfold more NRP-1 than their parental mouse mammary cells with epithelial character.

Recently, there is an upsurge in the development of potential therapeutics for the targeting and killing CSCs for the treatment of relapsing cancer. CSC has a prominent role in maintaining the relapsing and drug resistant phenotypes. Small molecule inhibitors are developed that are targeted mainly to developmental pathways such as sonic hedgehog, wnt, notch etc. which are perennially involved in the production of CSC, an analogue of normal stem cells (Lukaszewicz, A. I. et al. 2010, *J. Med. Chem.*, 53, 3439-3453). Liposomal delivery of differentiation inducing molecules such as retinoic acid is recently used as a concept to retard the onset of CSC-induced cancer relapse (Li, R. J. et al. 2011, *J. Controlled Rel.*, 149, 281-291). Immunoliposomes targeted to CSC surface markers are also used to target and treat CSC-induced cancer (Zhang, J. 2010, *J. Controlled Rel*, 18, 675-687).

Targeting and treating aggressive, drug resistant and relapsing condition of cancer, a trait followed by the cancer stem cells and their subclonal populations, is a challenging task. Efforts are underway to develop drug molecules targeting developmental pathways which are involved in the initiation of CSC.

Furthermore, there is no direct evidence of cationic lipid-based therapeutics against cancer stem cell (CSC). Cationic liposomes are used to deliver only genetic cargo to normal stem cells. The results are expected to be extrapolated for CSC as well, but no direct evidence is known. However, non-cationic liposomes are available for use against CSC. The main disadvantages of existing prior art for CSC are:
a) small molecular weight drugs that are designed to target CSC are mainly targeted to sonic hedgehog, wnt//β-catenin, Notch etc. developmental pathways which are potentially hazardous to target because it may pose non-specific collateral damages to normal developmental pathways;
b) Immunoliposomes uses antibody to target CSC membrane marker proteins and cannot logically differentiate between markers expressed on normal cells and CSC. These liposomes targeting CSC are mostly non-cationic in nature and hence gene carrying capacity is limited.

Therefore, keeping in view the hitherto prior art, a new synergistic composition has been developed for simultaneously delivering anti-cancer gene and small, hydrophobic (lipophilic) anticancer molecule to treat CSC-associated tumors and other aggressive tumors. The present invention is cationic lipid-based and it can carry dual cargo: drugs and genes simultaneously. Uniquely, it targets CSC via a non-developmental pathway i.e., through the cytoplasmic protein glucocorticoid receptor (GR) hence avoiding non specific collateral toxicity to normal developmental pathways and such a liposomal system is not known to target for the delivery of cargo to CSC. Targeting CSC or aggressive pancreatic cancer cells through this ubiquitous pathway makes the drug resistant cells more drug sensitive.

OBJECTIVES OF THE INVENTION

The main object of the present invention is to provide a synergistic anti-cancer composition for simultaneous gene therapy and drug delivery for cancer treatment and a process for the preparation thereof.

Another object of the present invention is to provide a synergistic anti-cancer composition for selective targeting to cancer cells.

Another object of the present invention is to provide a synergistic anti-cancer composition for simultaneous non-viral delivery of an anti-cancer drug and genetic material to glucocorticoid receptor expressing cancer cells, wherein said composition inhibits growth of breast or pancreatic tumor cells particularly aggressive cancer or Cancer-Stem-Cell (CSC)-like cells.

SUMMARY OF THE INVENTION

Accordingly, the present invention provides a synergistic anti-cancer composition for simultaneous non-viral delivery of an anti-cancer drug and genetic material to glucocorticoid receptor expressing cancer cells comprising:
  a) a cationic liposome;
  comprising of
    i. a cationic lipid preferably DODEAC (N,N-dihydroxyethyl, N,N-dioctadecyl ammonium chloride);
    ii. a neutral co-lipid preferably cholesterol;
    iii. dexamethasone for selective targeting of Glucocorticoid receptors; and
    iv. an anti-cancer drug
  wherein, the cationic lipid, the neutral co-lipid, dexamethasone and the anti-cancer drug are formulated in the range of 1:1:0.75:0.1 to 1:1:0.75:0.5.
  b) genetic material;
  wherein, the genetic material is complexed with the cationic liposome in the range of 1:2 to 1:8 molar charge ratio.

In one embodiment of the present invention synergistic composition inhibits growth of aggressive cancer or Cancer-Stem-Cell (CSC)-like cells.

In an embodiment of the present invention anti-cancer drug is selected from lipophilic drugs ESC8 (17 α-[3-(N, N-dioctyl,N-methyl-amino)-propan-1-yl]-17β-estradiol) and nutilin.

In another embodiment of the present invention genetic material is selected from the group consisting of antisense poly nucleotide RNA, antisense poly nucleotide DNA, genomic polynucleotide DNA, cDNA, mRNA, oligonucleotides, non-viral expression plasmids, silencing hairpin RNA (ShRNA) either individually or in combination thereof.

In still another embodiment of the present invention said genetic material is preferably non-viral expression plasmid containing cytotoxic genes, anti-metastatic genes, immune surveillance promoter genes, signaling pathway genes or cellular differentiation-inducing genes.

In still another embodiment of the present invention non-viral expression plasmid is preferably ShRNA encoding gene against signaling protein Neuropilin-1 (NRP-1).

In still another embodiment of the present invention cancer cells used are selected from group consisting of A549 (human lung), A498 (human renal), MiaPaca (human pancreas), ASPC-1 (human pancreas) and PANC-1 (human pancreas), ANV-1 (mouse breast CSC-like) cell lines.

In still another embodiment of the present invention ESC8 and nutilin concentration used is in the range of 1 μM to 20 μM.

In still another embodiment of the present invention it is administered to a subject via intra-venous, intra-muscular or intra-peritoneal route and wherein subject said is a mammal including human.

In still another embodiment of the present invention said composition is administered at a dose of 55-88 mg/Kg mice body-weight of a mixture composition, containing total lipid, drug and DNA, wherein the amount of drug as administered is 4-6.7 mg/Kg.

In still another embodiment of the present invention a process for the preparation of a synergistic anti-cancer composition for simultaneous non-viral delivery of an anti-cancer drug and genetic material, wherein the said process comprising the steps of:
  a) dissolving a cationic lipid, a neutral co-lipid, dexamethasone and an anti-cancer drug in a mole ratio in the range of 1:1:0.75:0.1 to 1:1:0.75:0.5 in a solvent preferably a mixture of methanol and chloroform (4:1 v/v) followed by removing solvent using nitrogen gas to obtain a lipid film;
  b) keeping the lipid film as obtained in step (a) under vacuum for a period ranging between 4 to 6 hours at a room temperature of 25-35° C. to obtain dried lipid film;
  c) hydrating the dried lipid film as obtained in step (b) by keeping dried film in 5% glucose solution for a period ranging between 10-12 hrs followed by vortexing for a period ranging between 1-2 min and bath sonicating for a period ranging between 2-3 min and probe sonicating for a period ranging between 2-3 min at temperature ranging between 25-30° C. to obtain liposomal formulation;
  d) mixing the liposomal formulation as obtained in step (c) with genetic material maintaining a molar ratio of liposomal formulation to genetic material in the range of 2:1 to 8:1 in serum free DMEM media followed by incubation at temperature in the range of 20-25° C. for 20-30 min with intermittent shaking at interval between 1-2 min to obtain a synergistic composition.

DETAILED DESCRIPTION OF THE INVENTION

Figure 1:
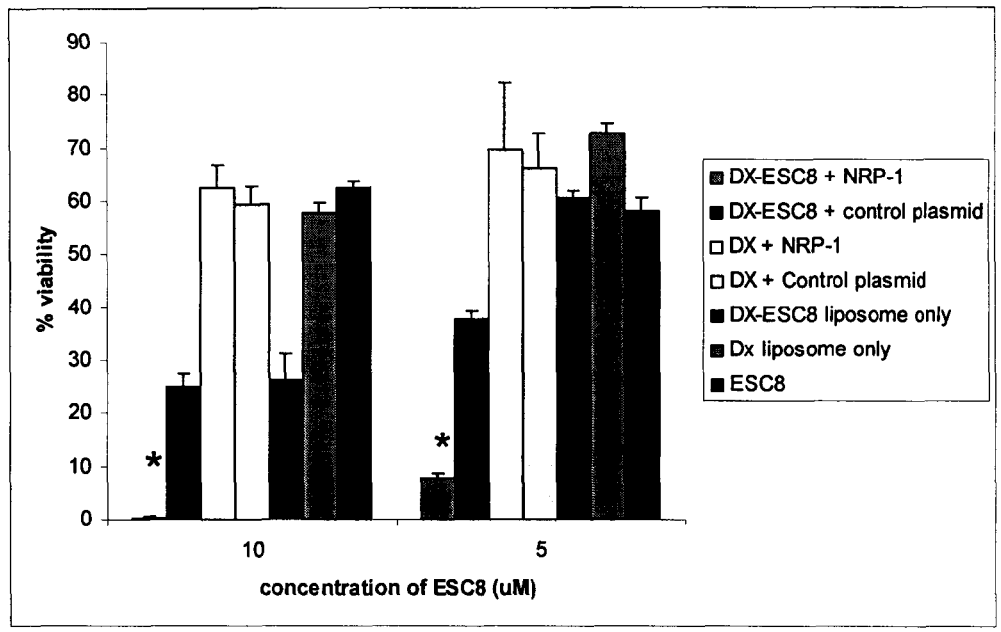
FIG. 1 shows the effect of DX-ESC8+NRP-1 ShRNA plasmid on ANV-1 breast cancer cells. Cells were treated for 48 h with a) DX-ESC8+NRP-1 ShRNA plasmid, b) DX-ESC8+control plasmid, c) DX+NRP-1 ShRNA plasmid, d) DX+control plasmids, e) DX-ESC8 liposome only, f) DX liposome only, g) ESC8, as free drug at the drug concentration of 10 or 5 μM in either naked or respective formulated state. The % of viabilities of treated cells (Y-axis) were calculated with respect to untreated cells [* denotes p<0.001 between DX-ESC8+NRP-1 group with other groups]

The abbreviations used in the invention are provided below.
amiR Artificial micro-RNA
CSC Cancer stem cell
Dex Dexamethasone
DO Refers to a composition of DODEAC and cholesterol
DODEAC N,N-dihydroxyethyl, N,N-dioctadecyl ammonium chloride
DO-ESC8 Refers to a composition of DODEAC, cholesterol and ESC8
DX Refers to a composition of DODEAC, cholesterol and dex
DX-ESC8 Refers to a composition of cationic lipid, cholesterol, dexamethasone and ESC8
EMT Epithelial-to-mesenchymal transition
ER Estrogen receptor
ESC8 17 α-[3-(N,N-dioctyl,N-methyl-amino)-propan-1-yl]-17β-estradiol
FCS Fetal Calf serum
GR Glucocorticoid receptor
GRE Glucocorticoid response elements
HIF-1 hypoxia inducible factor
Id-1 Inhibition of differentiation
mdr Multiple drug resistant
MET Mesechymal to Epithelial Transition
MMC Mouse mammary cells
NRP-1 Neuropilin-1
pGp p-glycoprotein
ShRNA silencing hairpin RNA In the present invention, a new potent synergistic anti-cancer has been developed from a cationic liposome by physically associating another anti-cancer agent in the lipid layer. The same lipid-based formulation being cationic in property also serves as a gene carrier and associates anti-cancer gene by electrostatic interaction for the purpose of gene delivery. This provides not only distinct improvement in the anti-cancer efficiency of the composition over the individual use of either the anti-cancer agent or the gene but showed exceptionally efficient killing of highly aggressive pancreatic and breast cancer cells ubiquitously expressing glucocorticoid receptors (GR). The formulation simultaneously facilitates drug and gene delivery to GR-expressing cells as well as helps increasing cell number receiving drug and genetic cargo.

In the invention, genes which can induce cell death are delivered via a non-viral route in combination with anti-cancer drug in order to provide better tumor remission and more effective prevention of tumor recurrence, thus leading to improved patient survival. A glucocorticoid pharmacological agent, dexamethasone is incorporated with the non-viral gene carrier i.e. cationic lipid coat. Dexamethasone, one of the most potent synthetic glucocorticoid, at mole ratios up to 3 compared to the cationic lipid, has been shown to facilitate the non-viral delivery of a variety of genetic constructs capable of performing their function (including apoptotic cell death) in human cancer cells.

A previously known formulation DX was prepared based on the idea that dexamethasone possesses close structural resemblance with cholesterol (a commonly used co-lipid in many cationic lipid formulations used for non-viral based gene delivery). Hence, it can be accommodated in cationic lipid formulation along-side cholesterol. It has also been shown that the lipid content of this formulation DX, upon treatment to cells lead to selective localization in cancer cells' nuclei only. But importantly, no nuclear localization of lipid content was observed in non-cancer cells. (Mukherjee, A. and Banerjee, R. Indian Application No. 1936/DEL/2006 and PCT/IN2007/000367, EP-2061514-A2 and Mukherjee, A. et al. 2009, *Mol Ther.*, 17, 623-631).

This observation of nuclear delivery of lipid content selectively to cancer cells led to reformulation of DX by associating a lipophilic anti-cancer drug in the lipid phase.

In the invention, any drug especially lipophilic anti-cancer drug which can induce cell death may be incorporated in the DX formulation as a mean to induce killing of cancer cell via, for example, apoptosis or sensitizing aggressive and relapsing cancer phenotypes to drug treatment. Here, different classes of anti-cancer pharmacological agents may be incorporated with a variable ratio with respect to other lipid-phase components. The non-limiting examples are as follows: a) drugs that act on DNA topoisomerases; b) DNA-alkylating agents; c) drugs acting on transcription machinery, d) drugs reactivating apoptotic proteins such as p53, etc. The anti-cancer drug may be preferably lipophilic in nature. A potent anti-cancer estrogen-structure-based drug, ESC8 (17 α-[3-(N,N-dioctyl,N-methyl-amino) propan-1-yl]-17β-estradiol), a lipophilic drug, was selected to be incorporated into DX. ESC8 kills human breast cancer cells with high selectivity irrespective of its estrogen receptor (ER)-expression status (Reddy, B. S., and Banerjee, R. Indian patent Application No. 0278/DEL/2007 and PCT/IN-07/00615; U.S. Pat. No. 8,012,952; Sinha, S. et al. 2011, *Mol. Cancer Res.*, 9, 364-374).

In the invention, genetic material to be combined along with dexamethasone associated cationic liposome carrying an anti-cancer agent, is selected from group consisting of antisense poly nucleotide RNA, antisense poly nucleotide DNA, genomic polynucleotide DNA, cDNA, mRNA, oligonucleotides, non-viral expression plasmids, silencing hairpin RNA (ShRNA) or combination thereof. First, cytotoxic genes such as tumor necrosis factor alpha or the tumor suppressor gene p53, which promotes apoptosis, can be provided. Second, genes which sensitize cells by enzymatically activating pro-drugs can be provided. For example, thymidine kinase or cytosine deaminase which respectively activates the cytotoxic pro-drugs gancylclovir and 5-fluorocytosine could be provided. Third, genes which promote immune surveillance could be provided. For example, tumor necrosis factor could be provided in combination with interleukin-2 and interferon-gamma. Fourth, anti-metastatic genes, such as 5 E1A, NM23 etc genes could be provided. Fifth, signaling pathway genes could be included which can either induce differentiation or reduce factors inhibiting differentiation of cancer-stem-cell (CSC) like cells leading to dedifferentiation of cells to less aggressive or drug sensitive conditions. Sixth, this formulation can be used for targeted down-regulation of a vital protein such as Hsp90, which is linked to multiple cancer implicated proproliferative factors. This can be accomplished by delivering artificial micro-RNA (amiR) against Hsp90-encoded plasmids using this formulation. We have recently shown that DX formulation can be conveniently used to deliver amiR-Hsp90 to selectively down-regulate Hsp90 and many of its proproliferative client proteins in cancer cells and tumor mass [Pore et al. *Biomaterials*, 2012, DOI: 10.1016/j.biomaterials.2013.05.054].

Treating highly aggressive, drug resistant and relapsing cancer, an identity trait of cancer stem cells, is a challenge with any existing treatment regimen. The novelty of the present invention lies in targeting and killing cancer stem cell (CSC)-like cells via GR pathway. The inclusion of anticancer drug ESC8 in the glucocorticoid receptor (GR)-targeted liposomal formulation DX along with simultaneous delivery of cellular differentiation-inducing gene (NRP-1 shRNA) or any anticancer gene is the key constructional feature that imparts the characteristic novelty by killing drug resistant breast cancer stem cell (CSC)-like cells and pancreatic cancer cells. This anticancer effect against these aggressive and drug resistant cells was not observed when these components are not simultaneously associated in the formulation or by the individual treatment of known anti-cancer drugs and anti-cancer genes.

Prior art shows the development of CSC-targeted drug molecules or therapeutic regimens targeting the CSC developmental pathways which is potentially hazardous because such therapeutics may non-specifically target the normal developmental pathways in vivo leading to unwanted toxicity. This is completely avoided by targeting through cancer cell-associated Glucocorticoid receptor (GR) mediated delivery of drug and genetic cargo simultaneously to cancer stem cell (CSC) in the present invention.

CSC-like cancer cells having undergone Epithelial-to-Mesenchymal Transition (EMT) are highly drug resistant and are usually having very pronounced and active p-glycoprotein (pGp)-based cytoplasmic efflux machinery and/or expressing multiple drug resistant (mdr) genes. Using these machineries drug resistant CSC-like cells can efflux out drugs entering their cytoplasm leaving the effective cellular drug concentration low. Since the formulation of the present invention is effective in delivering lipid-cargo inside cancer cells' nuclei, at least a fraction of lipid cargo can evade the p-Gp-based efflux machinery and reach the nuclei. Drugs that can activate suppressed anticancer factors residing in cancer cells nuclei can also be used in this formulation. Although the mechanism of action is not deciphered yet, but the effective drug concentration (even in fractions) in nucleus is potentially causing the reversal of drug resistance.

Therefore, the present invention relates to development of a new composition that contains ESC8 in the lipid layer of GR-targeting formulation, DX. The final liposomal solution, DX-ESC8, contains dexamethasone, ESC8, cholesterol and DODEAC. DX-ESC8 formulation upon electrostatically complexed with non-viral expression plasmid comprising ShRNA encoding gene against Neuropilin-1 (NRP-1) kills the aggressive cancer cells especially the breast cancer cells. ESC8 individually has very limited effect to the specific cancer cells such as CSC character bearing ANV-1 cells. However, when formulated in this composition, ESC8 showed significant anticancer effect. The effect is synergistically affected by the delivery of relevant gene encoded by ShRNA against NRP-1—in the same composition. NRP-1 is up-regulated during EMT leading to the up-regulation of a factor (ID-1) that inhibits differentiation of CSC-like cells, which infuses drug resistance character in CSC-like cells. Upon delivery of shRNA against NRP-1 the cells dedifferentiate by Mesechymal to Epithelial Transition (MET) with eventual down-regulation of ID-1. This resulted in concomitant decrease in drug resistivity and the co-administered drug, ESC8 could induce the killing of these CSC-like cells very effectively.

Furthermore, the silencing of neuropilin-1 was shown to have long term effect in maintaining the reduced aggressiveness in ANV-1 inoculated cancer in mouse tumor model. The composition was used to deliver ESC8 and shRNA plasmid against NRP-1. The idea was to achieve simultaneous knockdown of NRP-1, leading to inhibition of the expression of a factor called, Inhibition of differentiation (Id-1), which would finally lead the CSC cells to undergo partial MET and the production of differentiated cancer cells sensitive to anti-cancer agents. The breast cancer cells exhibiting CSC-like behavior and epitomizing breast cancer relapsing model was killed totally and the tumor volume was kept efficiently reduced until the injections were stopped. Any visible toxicity to mice repeatedly injected with the novel formulation DX-ESC8 in electrostatic combination with NRP-1 ShRNA encoding plasmid DNA was not noticed.

This formulation is also effective in the treatment of other aggressive cancers such as pancreatic cancer. It has been noticed that the drug molecule, ESC8 upon treatment as a naked drug exhibited no anticancer effect against pancreatic cancer cells, PANC-1 and ASPC-1. However, in association with GR-targeted formulation DX, the drug killed aggressive pancreatic cancer cells very efficiently irrespective of the kind of plasmid used in the lipid-DNA complex. This may be attributed to the fact that NRP-1 is not an important target for pancreatic cancer. Hence, no extra anti-cancer effect was observed by using NRP-1 ShRNA plasmid. Other anti-cancer genes, implicated with pancreatic cancer can be conveniently used to get effective synergism. Also, it is assumed that the mouse NRP-1 shRNA plasmid has been used, which possibly has no effect on human cancer cells. But, it is to be noted that the cells are becoming very sensitive to the drug entrapped in the formulation especially when the naked drug has no anti-cancer effect.

Furthermore, in order to broaden the utility of the DX-associated formulation, DX has been reformulated with another known drug nutilin (in place of ESC8). Nutilin inhibits the interaction of p53 with mdm2. This lead to reactivation of p53 which initiates apoptosis thereby killing the highly proliferating cancer cells.

EXAMPLES

The following examples are given by way of illustration therefore should not be construed to limit the scope of the present invention.

| MATERIALS AND METHODS | |
|---|---|
| MATERIALS USED | SOURCE |
| ANV-1 | Kind gift from Dr. Keith L Knutson, Department of Immunology, Mayo Clinic, USA. It can be obtained from Mayo Clinic cell line repository and is a Mayo Clinic property. It is deposited as 'ANV-1'. The cell line is already published [Santisben et al. Cancer Research (2009) 69, 2887-2895] and is available publicly for research purposes only upon request. |
| female mice of FVB strain | NCI-Frederick, MD |
| NRP-1 shRNA Plasmid with targeting sequence mNRP1sh3 | Open Biosystems, Huntsville, Ala, cat no. TRCN0000029861 |
| Nutilin-3 | Cayman Chemicals, Catalogue no: 18585-20000040 |
| PANC-1, A549, MiaPaca-2, A498 and ASPC-1 | ATCC, USA; Cat. No. PANC-1 (CRL-1469), A549 (CCL-185), MiaPaca-2 (CRL-1420), A-498 (HTB-44) and ASPC-1 (CRL-1682) |

Cell Lines

ANV-1, PANC-1 and ASPC-1 cells were maintained in RPMI 1640 containing 10% fetal bovine serum (FBS), 1% penicillin/streptomycin, 1% sodium pyruvate, 2.5% HEPES, and 2 mM L-glutamine. The PANC-1, A549, MiaPaca, A498 and ASPC-1 were obtained from American Type Tissue Culture (ATCC, USA). ANV-1 was obtained as a kind gift from Dr. Keith L Knutson, Department of Immunology, Mayo Clinic, USA and is now obtained from Mayo Clinic cell line repository.

NRP-1 shRNA Plasmid

The plasmid for mouse NRP-1 shRNA was purchased from Open Biosystems, Huntsville, Ala. The targeting sequences for mNRP-1 is 5' CCA GAG AAT CAT AAT CAA CTT-3'(mNRP1sh3; SEQ ID NO;1).

Example 1

Preparation of Liposome Formulation and Complexation with NRP-1 ShRNA Plasmid

DODEAC (N,N-dihydroxyethyl N,N-dioctadecyl ammonium chloride, the cationic lipid) (0.645 µg), cholesterol (the co-lipid) (0.386 µg), dexamethasone (another co-lipid and a GR-targeting synthetic ligand) (0.294 µg) and ESC8 (anti-cancer drug) (151 µg) were premixed in a molar ratio of 1:1:0.75:0.25 in chloroform and methanol (4:1 v/v) (1 ml). The organic solvent was removed under a thin flow of dry air/$N_2$ to get a thin layer of lipid film. The lipid film was further dried under high vacuum for 5 hrs at 27° C. The dried film was hydrated using 1 ml 5% glucose solution and kept overnight at room temperature. The solution was vortexed and then sonicated under titanium probe at a continuous output level of 4 for a total of 3 minutes or more until all the lipids are suspended in solution with intermittent stops of 5 seconds after every 16 seconds of sonication. The resulting liposome formulation was named DX-ESC8, which contained cationic lipid, cholesterol, dexamethasone and ESC8 as 1 mM: 1 mM: 0.75 mM: 0.25 mM. Similarly, when ESC8 was not mixed to other constituent lipids, the resulting formulation was called DX [DODEAC: Cholesterol: dexamethasone, 1:1:0.75 molar ratio]. A control liposome formulation DO was made wherein only DODEAC and cholesterol were taken in 1:1 molar ratio. Another control liposome DO-ESC8 was made wherein DODEAC, cholesterol and ESC8 were taken in 1:1:0.25 molar ratio. These liposomal formulations were mixed with a fixed amount of neuropilin (NRP)-1 ShRNA encoding plasmid (typically, 0.3 µg per well of 96 well plate) or control plasmids (0.3 µg per well of 96 well plate in serum free DMEM media (100 µl) following our previously optimized protocol [Mukherjee and Banerjee 2006, 2007; Mukherjee et. al 2009]. Briefly, liposomes (14 µl or 7 µl formulation containing 1 mM cationic lipid concentration) were respectively mixed to 0.3 µg DNA in serum free DMEM medium (100 µl). The resultant solutions were incubated for 20 min with intermittent shaking to make stable lipid: DNA complex (lipoplex) at room temperature. DX-ESC8 complexed with NRP-1 Sh-RNA containing plasmid is referred as DX-ESC8+NRP-1 hereafter.

Example 2

Preparation of DX-Nutilin Liposome Formulation and Complexation with NRP-1 ShRNA Plasmid DODEAC (N,N-dihydroxyethyl N,N-dioctadecyl ammonium chloride, the cationic lipid) (645 µg), cholesterol (the co-lipid) (386 µg), dexamethasone (another co-lipid and a GR-targeting synthetic ligand) (294 µg) and nutilin (anti-cancer drug) (154.4 µg) were premixed in a molar ratio of 1:1:0.75:0.25 in chloroform and methanol (4:1 v/v) (1 ml). The organic solvent was removed under a thin flow of dry air/$N_2$ to get a thin layer of lipid film. The lipid film was further dried under high vacuum for 5 hrs at 27° C. The dried film was hydrated using 1 ml 5% glucose solution and kept overnight at room temperature. The solution was vortexed and then sonicated under titanium probe at a continuous output level of 4 for a total of 3 minutes or more until all the lipids are suspended in solution with intermittent stops of 5 seconds after every 16 seconds of sonication. The resulting liposome formulation was named DX-nutilin, which contained cationic lipid, cholesterol, dexamethasone and nutilin as 1 mM: 1 mM: 0.75 mM: 0.25 mM. Similarly as discussed before, when nutilin was not mixed to other constituent lipids, the resulting formulation was called DX [DODEAC: Cholesterol: dexamethasone, 1:1:0.75 molar ratio]. These liposomal formulations were mixed with a fixed amount of neuropilin (NRP)-1 ShRNA encoding plasmid (typically, 0.3 µs per well of 96 well plate) or control plasmids (0.3 µg per well of 96 well plate in serum free DMEM media (100 µl) following our previously optimized protocol [Mukherjee and Banerjee 2006, 2007; Mukherjee et. al 2009]. Briefly, liposomes (14 µl or 7 µl formulation containing 1 mM cationic lipid concentration) were respectively mixed to 0.3 µg DNA in serum free DMEM medium (100 µl). The resultant solutions were incubated for 20 min with intermittent shaking to make stable lipid: DNA complex (lipoplex) at room temperature. DX-nutilin complexed with NRP-1 Sh-RNA containing plasmid is referred as DX-nutilin+NRP-1 hereafter.

Example 3

In-Vitro Cell Culture Study

Cancer cells (ANV-1, PANC-1, ASPC-1) were inoculated at a concentration of 5000 cells/well of 96-well cell culture plates in 10% Fetal Calf serum (FCS) containing DMEM media. Following an incubation of minimum of 16 h at 37° C., the cells were treated in triplicate with respective lipoplexes (DX-ESC8, DO-ESC8, DX,) pre-complexed with 0.3 µg of NRP-1 or control plasmid amounts per well as discussed in Example 1. The cells were also treated with naked liposomes with or without ESC8 or free drug, ESC8, in a final volume of 300 µl (volume made up with 10% FCS containing DMEM media) continuously for 48 h (mostly) or 72 h. The test solutions were picked from the following list: a) DX-ESC8 pre-complexed with 0.3 µg of NRP-1 Sh-RNA plasmid, b) DX-ESC8 pre-complexed with 0.3 µg control plasmid, c) DO-ESC8 with 0.3 µg NRP-1 Sh-RNA plasmid, d) DO-ESC8 with 0.3 µg control plasmid, e) DX liposome pre-complexed with 0.3 µg NRP-1 Sh-RNA plasmid, f) DX liposome pre-complexed with 0.3 µg control plasmid, g) DO liposome pre-complexed with 0.3 µg NRP-1 Sh-RNA plasmid, h) DX-ESC8 liposome only, i) DX-liposome only, j) DX liposome pre-complexed with NRP-1 Sh-RNA plasmid followed by ESC8 addition, k) only ESC8 addition. Thereafter cells were assayed for viability using MTS assay kit (Promega) following manufacturer's protocol.

For cells treated with DX-nutilin, the test solutions were: a) DX-nutilin pre-complexed with 0.3 □g of NRP-1 Sh-RNA plasmid, b) DX-ESC8 pre-complexed with 0.3 □g control plasmid, c) DX liposome pre-complexed with 0.3 □g NRP-1 Sh-RNA plasmid, d) only ESC8 addition.

Example 4

In-Vivo Tumor Model Study $1.5 \times 10^5$ ANV-1 cells were orthotopically injected into mammary fat pad of female mice of FVB strain (NCI-Frederick, Md.). Two weeks following the tumor cell inoculation, when the average tumor sizes were 50 mm$^3$, the mice were injected intraperitoneally either with: a) 5% glucose (as untreated group), b) DX-ESC8 pre-complexed with 50 µg of NRP-1 Sh-RNA plasmid (referred as DX-ESC8+NRP-1 hereafter), or c) DX-ESC8 pre-complexed with 50 µg of control plasmid. DX-ESC8+NRP-1 was also injected in a separate group of mice when the average tumor size was 330 mm$^3$. Five injections were given to respective groups at a space of 2-3 days. The tumors were measured twice a week. Tumor volumes were calculated as ½(ab$^2$), where 'a' is the length and 'b' the breadth of tumor. For in vivo study, the lipid/DNA composition was as follows: a) plasmid DNA amount 50 µg per mice; b) 4-8 mole equivalent amount of DX-ESC8 formulation. Typically, we used 6 mole equivalent of lipid formulation with respect to DNA. When the DNA amount is 50 µg (i.e, 0.1515 µmole), the number of moles and hence amounts of lipid, colipid, dexamethasone and drug (ESC8) in DX-ESC8 are, DODEAC (0.909 µmole, 547 µg), cholesterol (0.909 µmole, 350 µg), dexamethasone (0.681 µmole, 267.5 µg) and ESC8 (0.227 µmole, 98.8 µg). Hence, each tumor-bearing mouse gets a dose of 1.263 mg of DX-ESC8 and 50 µg of DNA. Considering each mouse of 20 mg body weight a total lipid/DNA content injected is about 66 mg/Kg of body weight, wherein ESC8 amount injected is about 5 mg/Kg.

Example 5

FIG. 1 demonstrates that the simultaneous delivery of NRP-1 sh-RNA and ESC8 (i.e., DX-ESC8+NRP-1) had maximum anticancer effect towards ANV-1 breast cancer cells with CSC-like property. It is notable that the treatment with naked drug in respective concentration had the least anticancer effect under same condition. However, when ESC8 was delivered separately along with a control plasmid using the same protocol, this ESC8-control formulation showed moderate anticancer effects. Other control treatments such as, when ESC8-free lipoplexes [DX +NRP-1 and DX+control plasmid] or when the DX-ESC8 liposome formulation [DX-ESC8 liposome only] or DX liposome alone, had much lesser anticancer effect than DX-ESC8+NRP-1 treatments. This indicates that the DX-formulation should contain the naked drug constitutively in it to show maximum anti-cancer effect to the breast cancer cells and there may be a synergism of anti-cancer effect when neuropilin-1 is concomitantly knocked down. As is evident from the figure, the viability of ANV-1 cells treated with DX-ESC8-NRP-1 was 0-10% as opposed to the viability of cells treated independently with DX-ESC8 liposome (70% viability) or ESC8 (60-70% viability). It clearly shows that the synergism exists only when DX-ESC8 was pre-complexed with NRP-1 sh-RNA plasmid. The anticancer effect was evident from 3 h onwards of treatment of DX-ESC8-NRP-1 lipoplex. The naked drug had no visual effect on cells in shorter treatment time. However, for 48 h or more of treatment some of the cells showed signs of mortality. We observed that at least 50 µM ESC8 free drug treatment for 72 h was needed to get 95-100% of ANV-1 cell killing. Concentration-wise this was 10 fold more than the ESC8 concentration in DX-ESC8-NRP-1 lipoplex.

Figure 2:
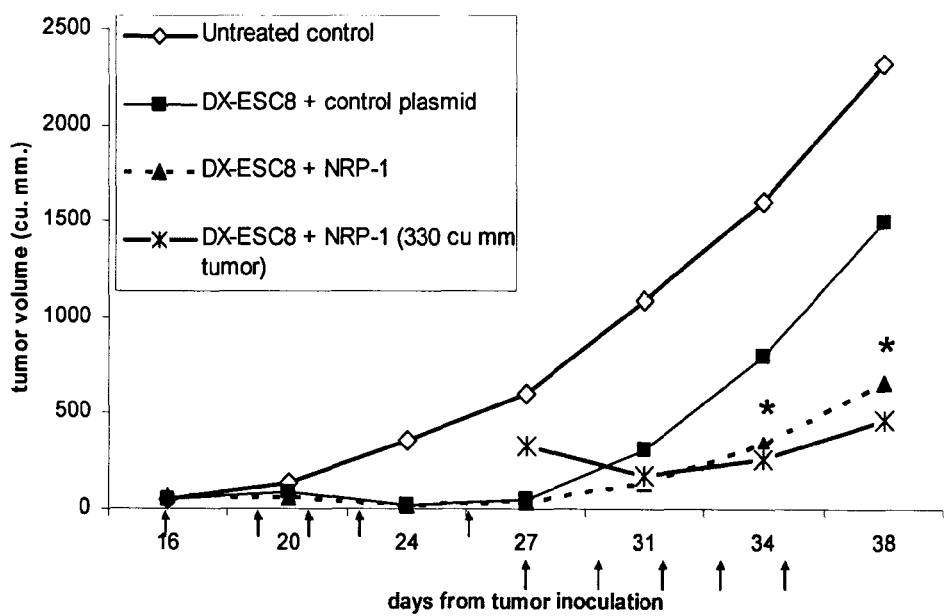
FIG. 2 shows the effect of DX-ESC8+NRP-1 ShRNA plasmid on ANV-1 tumor model. Mice with tumors in mammary fat fad were segregated in four groups. Three groups with average tumor size 45-50 mm³ were treated as following, a) 5% glucose (untreated control, white diamond), b) DX-ESC8+control plasmid (black square), c) DX-ESC8+NRP-1 ShRNA plasmid (black triangle). Black arrow heads depict the days of injections. For the fourth group, DX-ESC8+NRP-1 ShRNA plasmid was injected when average tumor size became 330 mm³ (red star). Red arrows indicate the days of injections for the fourth group. (n=5). [* denotes p<0.05, between ESC8-NRP and ESC8-control].

FIG. 2 shows a line graph depicting the result of an in vivo study on ANV-1 tumor model in mice. ANV-1 tumors were generated by orthotopic inoculation of these cells in mammary fat pad of mice. Two weeks following cell inoculation, when the average size of tumor was ~50-60 mm$^3$, intraperitoneal injections of respective lipoplex formulations, i.e., DX-ESC8+NRP-1 sh-RNA plasmid or DX-ESC8+control plasmid were started. FIG. 2 shows that both the treatment regimens had highly effective anti-cancer effect and could equally prevent the aggressiveness of the tumor in the initial days when the injections were on. However, at the later stage when no more injections were given the tumor size began to increase but with a much controlled rate for DX-ESC8+NRP-1 treatment group than in DX-ESC8+control plasmid group. A significant difference of tumor sizes was evident between DX-ESC8+NRP-1 and DX-ESC8+control plasmid groups. In another group of mice when the average tumor size was 330 mm$^3$, intraperitoneal injections of DX-ESC8+NRP-1 started. The inhibition of aggressiveness of this big sized tumor was clearly observed within a day of 1$^{st}$ injection. Experiment was terminated when the average tumor sizes of untreated control group exceeded 2000 mm$^3$.

Figure 3A:
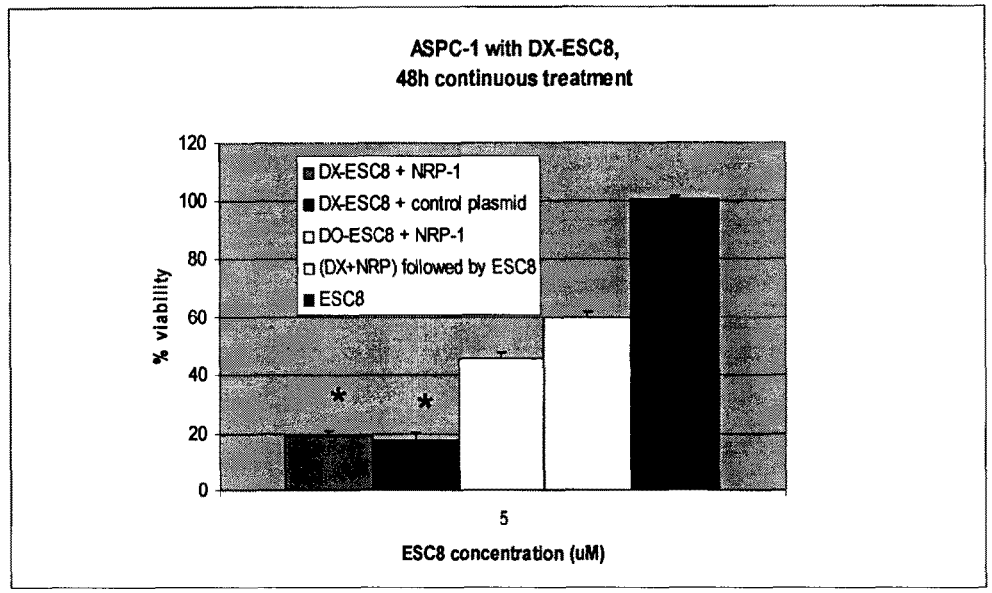
FIG. 3A shows the effect of DX-ESC8+NRP-1 ShRNA plasmid on ASPC-1 pancreatic cancer cells. Cells were treated for 48 h with a) DX-ESC8+NRP-1 ShRNA plasmid, b) DX-ESC8+control plasmid, c) DO-ESC8+NRP-1 ShRNA plasmid, d) DX+NRP-1 ShRNA plasmid, followed by ESC8 treatment e) ESC8, as free drug at the drug concentration of 5 μM in either naked or respective formulated state. The % of viabilities of treated cells (Y-axis) were calculated with respect to untreated cells [* denotes p<0.01 between DX-ESC8 lipoplex groups with other groups].
Figure 3B:
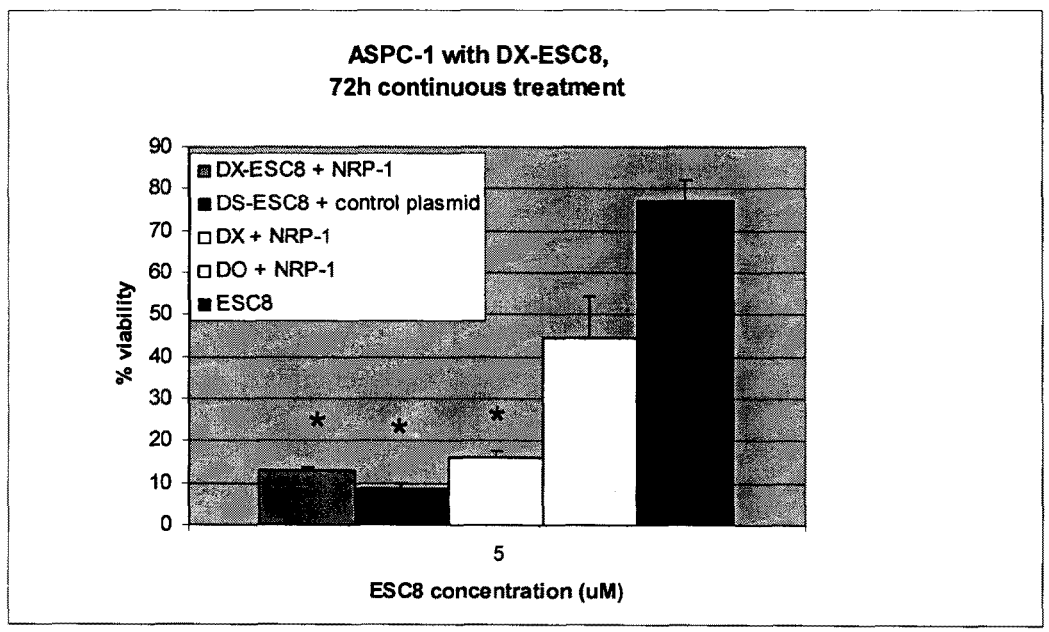
FIG. 3B shows the effect of DX-ESC8+NRP-1 ShRNA plasmid on ASPC-1 pancreatic cancer cells. Cells were treated for 72 h with a) DX-ESC8+NRP-1 ShRNA plasmid, b) DX-ESC8+control plasmid, c) DX+NRP-1 ShRNA plasmid, d) DO+NRP-1 ShRNA plasmid e) ESC8, as free drug at the drug concentration of 5 μM in either naked or respective formulated state. For groups c and d the liposome concentrations of DX or DO were equivalent to the corresponding liposome concentration in DX-ESC8 containing 5 μM ESC8. The % of viabilities of treated cells (Y-axis) were calculated with respect to untreated cells [* denotes p<0.01 between DX-ESC8 lipoplex groups or DX+NRP-1 ShRNA plasmid group with other groups].

FIG. 3 shows bar graphs depicting the effect of DX-ESC8+NRP-1 treatment on pancreatic cancer ASPC-1 cells. FIGS. 3A and 3B shows that DX-ESC8 complexed with NRP-1 ShRNA plasmid [i.e. DX-ESC8+NRP-1] had the maximum killing effect to pancreatic cancer ASPC-1 cells compared to other prepared formulations after 48 h (FIG. 3A) or 72 h (FIG. 3B) of continuous treatment. The DX-ESC8 lipoplex containing control plasmid [DX-ESC8+control plasmid] however in this cell line showed similar anticancer effect as that of the group represented by DX-ESC8+NRP-1. In FIG. 3A It is notable that when ESC8 was not premixed with DX and was added after the treatment of DX-NRP-1 complex [i.e., the group indicated by (DX-NRP) followed by ESC8], there was only about 40% toxicity to the cells. This clearly indicates that to maximize the killing effect of the formulation, the anti-cancer molecule has to be constitutively associated with DX formulation. Moreover, the naked drug has the least toxic effect to the cells. In overall, the data indicates that co-formulation of DX and ESC8 when co-complexes with any plasmid (NRP-1 ShRNA or control plasmid) it provides maximum anti-cancer effect to these pancreatic cancer cells. As is evident from the figure the cellular viability of pancreatic cancer cells decreased by 80% when treated with DX-ESC8 formulation pre-complexed with plasmids (NRP-1 sh-RNA or control) than when cells were pretreated with naked drug ESC8.

Figure 4:
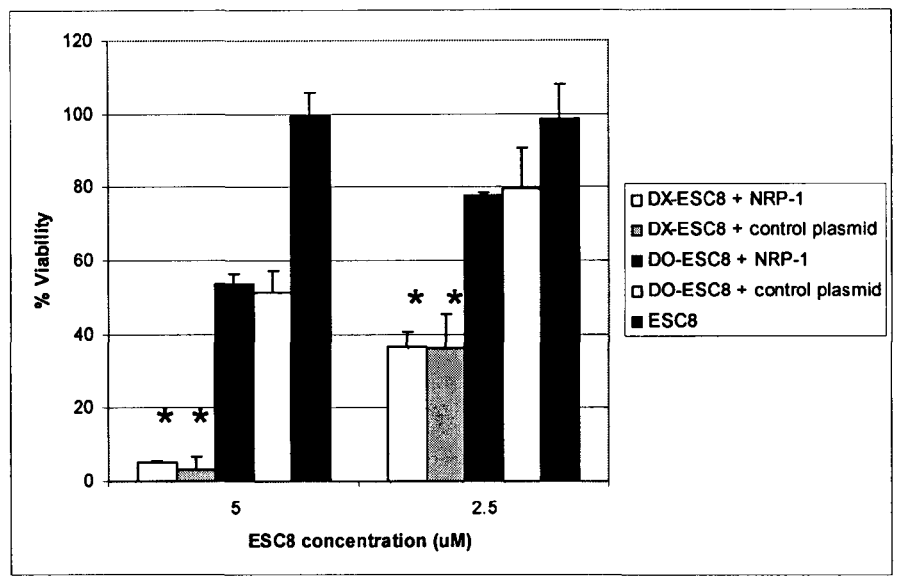
FIG. 4 shows the effect of DX-ESC8 ShRNA plasmid on PANC-1 pancreatic cancer cells. Cells were treated for 48 h with a) DX-ESC8+NRP-1 ShRNA plasmid, b) DX-ESC8+control plasmid, c) DO-ESC8+NRP-1, d) DO-ESC8+control plasmid e) ESC8, as free drug at the drug concentrations of 5 or 2.5 μM in either naked or respective formulated state. The % of viabilities of treated cells (Y-axis) were calculated with respect to untreated cells [* denotes p<0.01 between DX-ESC8 lipoplex groups with other groups].

FIG. 4 is a bar graph depicting the effect of DX-ESC8+NRP-1 on PANC-1 cells. As in case of the pancreatic cancer cell, ASPC-1 we see the similar anti-cancer effect of DX-ESC8 complexed with either NRP-1 ShRNA or Control plasmid in second pancreatic cancer cell, PANC-1. It is notable that when there was no dexamethasone in the lipoplex [i.e., DO-ESC8 complexed with either NRP-1 ShRNA or control plasmid] the anti-cancer effect diminishes. The naked drug ESC8 has no toxicity to the cancer cells at the given experimental condition. In overall, the data again indicates the importance of the constitutive association of ESC8 in the dexamethasone-associated cationic lipid formulation DX towards obtaining maximum anti-cancer effect.

Figure 5:
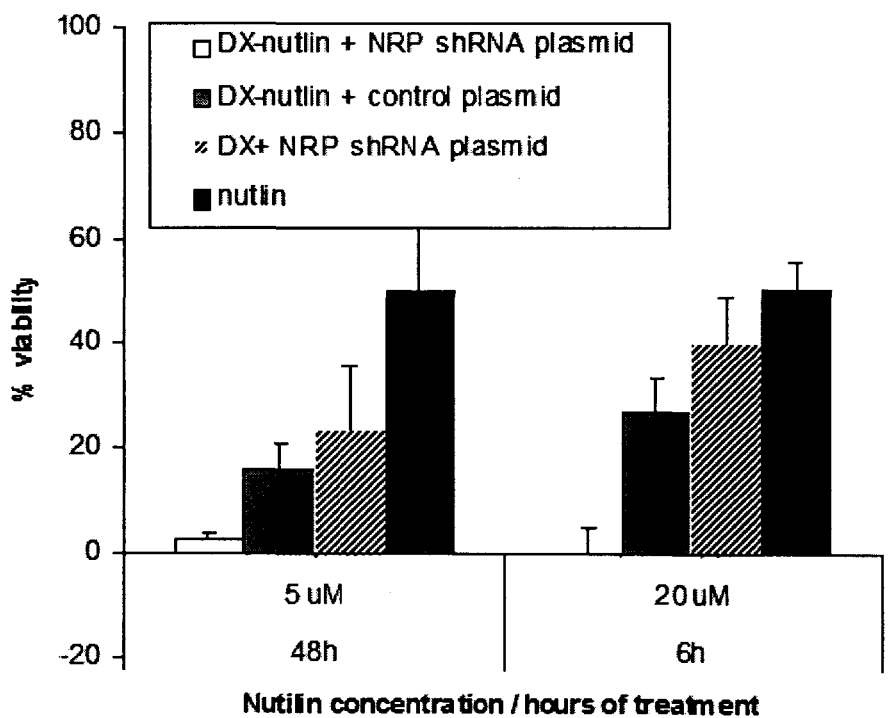
FIG. 5 shows the effect of DX-Nutilin+NRP-1 ShRNA plasmid on ANV-1 breast cancer cells. Cells were treated with a) DX-nutilin+NRP-1 ShRNA plasmid, b) DX-nutilin+control plasmid, c) DX+NRP-1 ShRNA plasmid, d) nutilin as free drug. The treatments were done in two different conditions, a) continuous treatment for 48 h by the respective formulations with 5 mM effective nutilin concentration; b) treatment for only 4 h by respective formulations with 20 mM effective nutilin concentrations. The % viabilities of treated cells (Y-axis) were calculated with respect to untreated cells.
Figure 6:
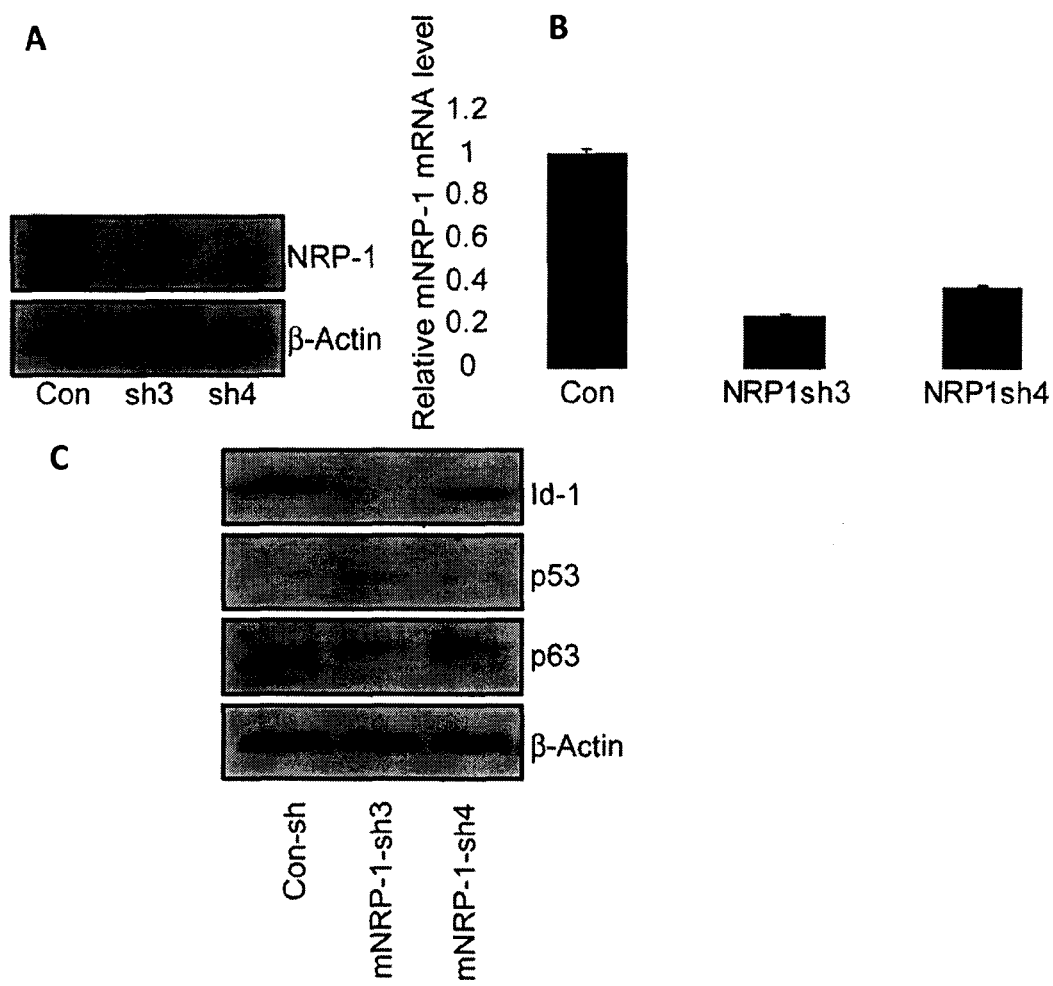
FIG. 6 shows the effect of mNRP-1 shRNAs on NRP-1 expression and on its client proteins in ANV-1 cells. It provides supporting data that the treatment of mNRP1-sh3 and mNRP1-sh4 to ANV-1 cells indeed down-regulates NRP-1 protein and m-RNA levels.
A. Western blot analysis for NRP-1 expression in cells following the respective treatments of shRNAs, mNRP-1-sh3 (sh3) & mNRP-1-sh4 (sh4). B. RT-PCR analysis to quantify the relative NRP-1 m-RNA expression following the respective treatments of NRP1sh3 and NRP1sh4 in ANY-1 cells. C. Western blot analysis to demonstrate the change in expression levels of Id-1, p53 and p63 proteins with respect to that of control shRNA (Con-sh) treated cells.
Figure 7:
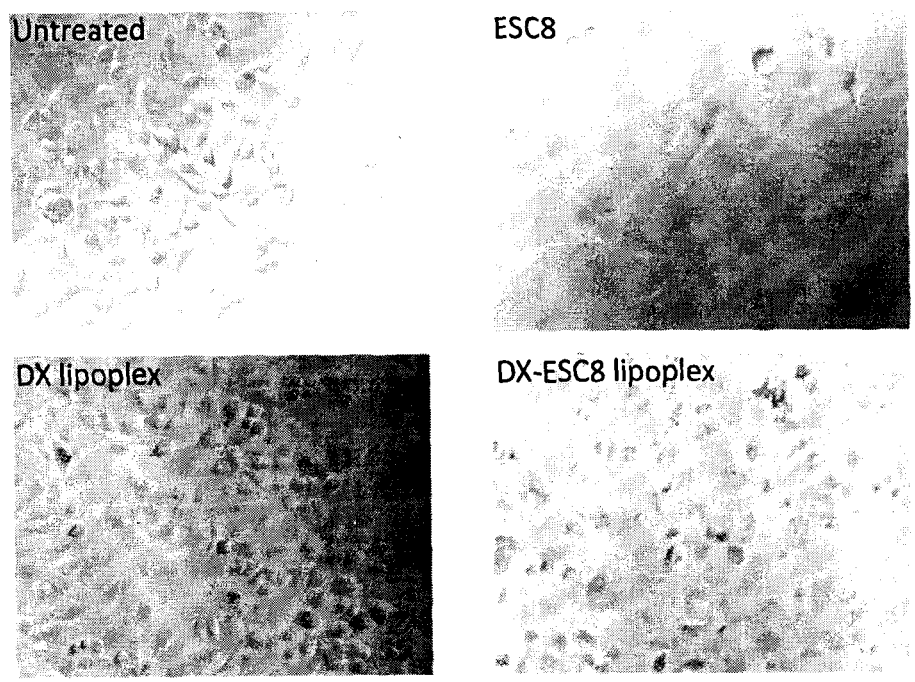
FIG. 7 shows the microscopic image demonstration to show the relative conditions of A549 (human lung cancer) cells with different treatments: A549 cancer cells in either untreated, ESC8-treated, DX-lipoplex (DX+DNA) treated or DX-ESC8 lipoplex treated condition. DX-ESC8 lipoplex visibly induced significantly high cytotoxicity in A549 cells compared to cells of other treatment groups.
Figure 8:
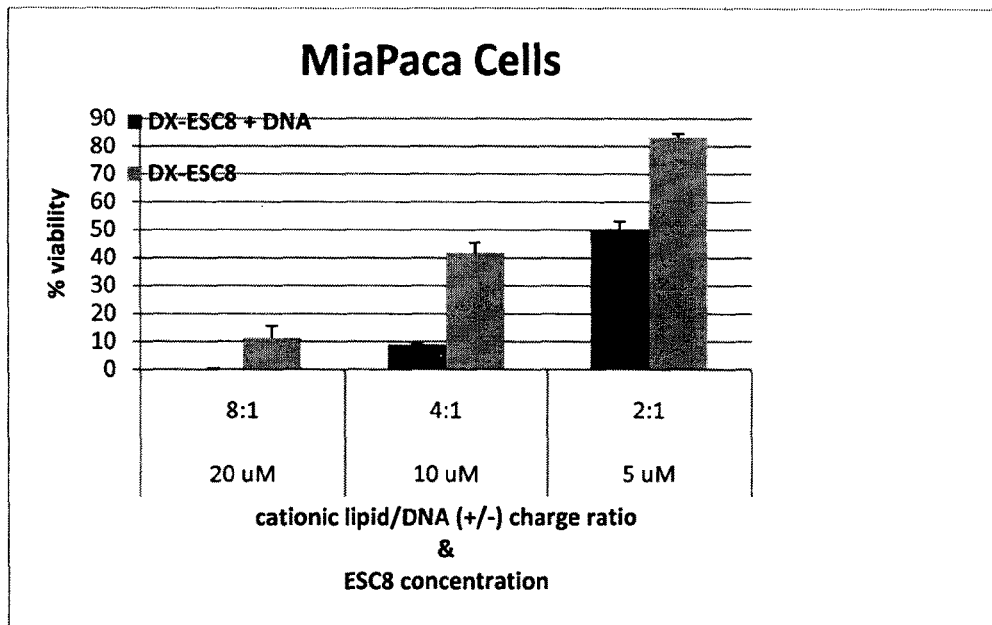
FIG. 8 shows the MTT-based viability studies to demonstrate the relative effect of 'DX-ESC8+DNA' lipoplex and liposome 'DX-ESC8' in MiaPaca (human pancreatic cancer) cells. a) different cationic lipid to DNA (+/−) charge ratios; b) different micromolar concentrations of ESC8. ESC8 as a naked drug shows only breast cancer selective cytotoxicity and usually exhibits least cytotoxicity in cells of non gynecological origin.
Figure 9:
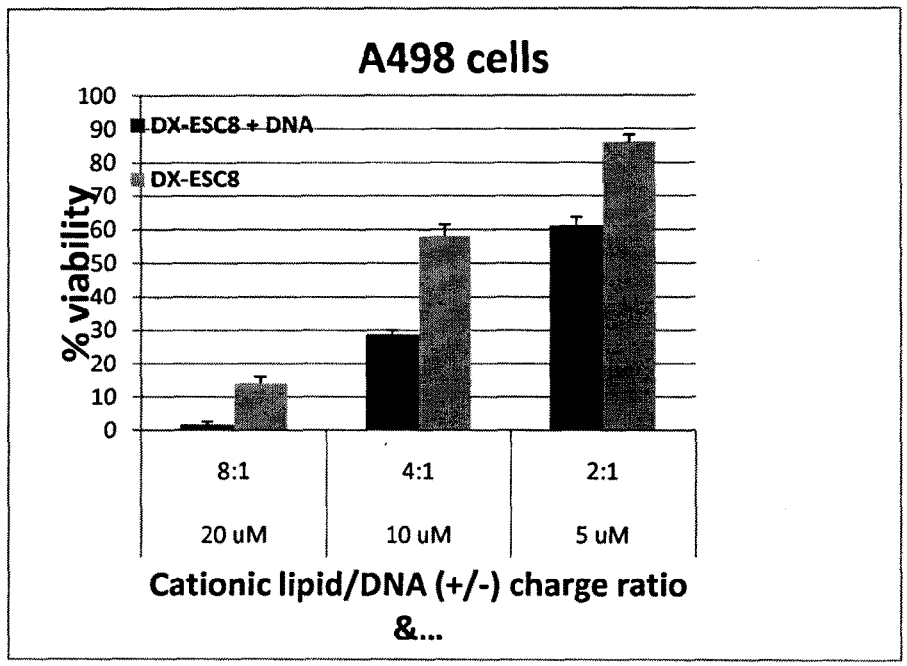
FIG. 9 shows MTT-based viability studies to demonstrate the relative effect of 'DX-ESC8+DNA' lipoplex and liposome 'DX-ESC8' in A498 (human renal carcinoma) cells. a) Different cationic lipid to DNA (+/−) charge ratios; b) different micromolar concentrations of ESC8. ESC8 as a naked drug shows only breast cancer selective cytotoxicity and usually exhibits least cytotoxicity in cells of non gynecological origin.

FIG. 5 is a bar graph depicting the effect of another lipophilic drug, nutilin, when co-formulated with DX. Nutilin acts in nucleus as it inhibits p53 interaction with pro-cancerous mdm2. This inhibitory interaction inhibits the degradation of pro-apoptotic protein p53 resulting in induction of apoptosis followed by killing of cancer cells. Herein, the resulting formulation of DX and nutilin i.e., DX-nutilin was pre-complexed with NRP-1 ShRNA plasmid and treated to ANV-1 cells. The final concentration of nutilin in the formulation as well as its time of treatment to ANV-1 cells were varied. It is clearly evident that the DX-nutilin+NRP-1 ShRNA plasmid potentiated more cancer cell killing than the individual treatments of DX-NRP-1, DX-nutilin+control plasmid and free drug, nutilin. In conclusion, the data indicates that potentially active, lipophilic drugs upon liposomally formulated with DX may lead to maximum anti-cancer effect.

Advantages Of The Invention

The process of the present invention can be exploited for preparing cationic lipid based drug and gene transfer reagents containing glucocorticoid receptor binding dexamethasone in the formulation.

The composition disclosed herein can be used to deliver a pharmacologically active drug molecule and a non-viral expression vector into cancer cells for therapeutic use.

The expression vectors can be used in gene therapy protocols to deliver a therapeutically useful protein to a cell or for delivering nucleic acids encoding therapeutically useful protein molecules.

The dexamethasone-associated lipid based formulation can be formulated with ionic/non-ionic and lipophilic therapeutic agents including anticancer agents such as ESC8, Taxol™, irinotecan, nutilin etc. therapeutic agent(s).

We claim:

1. A synergistic anti-cancer composition for simultaneous non-viral delivery of an anti-cancer drug and genetic material to glucocorticoid receptor expressing cancer cells comprising complexes comprising:
   a) a cationic liposome; comprising
      i. a cationic lipid;
      ii. a neutral co-lipid;
      iii. dexamethasone for selective targeting of Glucocorticoid receptors; and
      iv. a lipophilic anti-cancer drug;
   wherein, the cationic lipid, the neutral co-lipid, the dexamethasone and the lipophilic anti-cancer drug are formulated in the range of 1:1:0.75:0.1 to 1:1:0.75:0.5, and
   b) genetic material encoding a gene or antisense nucleic acid, the expression of which in tumor cells has an anti-tumor effect;
   wherein the genetic material is complexed with the cationic liposome in the range of 1:2 to 1:8 molar charge ratio, wherein the cationic lipid comprises DODEAC (N, N-dihydroxyethyl, N, N-dioctadecyl ammonium chloride) or the neutral co-lipid comprises cholesterol, and wherein the anti-cancer drug is ESC8 or nutilin.

2. The synergistic composition as claimed in claim 1, wherein the synergistic composition inhibits growth of aggressive cancer or Cancer-Stem-Cell (CSC)-like cells.

3. The synergistic composition as claimed in claim 1, wherein the anti-cancer drug is ESC8.

4. The synergistic composition as claimed in claim 1, wherein the genetic material is selected from the group consisting of antisense poly nucleotide RNA, antisense poly nucleotide DNA, genomic polynucleotide DNA, cDNA, mRNA, oligonucleotides, non-viral expression plasmids, silencing hairpin RNA (ShRNA) either individually or in combination thereof.

5. The synergistic composition as claimed in claim 4, wherein said genetic material comprises a non-viral expression plasmid containing cytotoxic genes, anti-metastatic genes, immune surveillance promoter genes, signaling pathway genes or cellular differentiation-inducing genes.

6. The synergistic composition as claimed in claim 1, wherein the cancer cells used are selected from group consisting of A549 (human lung), A498 (human renal), MiaPaca (human pancreas), ASPC-1 (human pancreas) and PANC-1 (human pancreas), and ANV-1 (mouse breast CSC-like) cell lines.

7. The synergistic composition as claimed in claim 1, wherein the ESC8 or nutilin concentration is in the range of 1 μM to 20 μM.

8. The synergistic composition as claimed in claim 1, wherein it is administered to a subject via intra-venous, intra-muscular or intra-peritoneal route and wherein subject said is a mammal including human.

9. The synergistic composition as claimed in claim 1, wherein said composition is administered at a dose of 55-88 mg/Kg mice body-weight of a mixture composition, containing total lipid, drug and DNA, wherein the amount of drug as administered is 4-6.7 mg/Kg.

10. The synergistic composition as claimed in claim 5, wherein the plasmid contains a ShRNA encoding gene against signaling protein Neuropilin-1 (NRP-1).

11. The synergistic composition as claimed in claim 1, wherein the cationic lipid comprises DODEAC (N, N-dihydroxyethyl, N, N- dioctadecyl ammonium chloride) and the neutral co-lipid comprises cholesterol.

12. A synergistic anti-cancer composition for simultaneous non-viral delivery of an anti-cancer drug and genetic material to glucocorticoid receptor expressing cancer cells comprising complexes comprising:
   a) a cationic liposome; comprising
      i. a cationic lipid;
      ii. a neutral co-lipid;
      iii. dexamethasone for selective targeting of Glucocorticoid receptors; and
      iv. a lipophilic anti-cancer drug;
   wherein, the cationic lipid, the neutral co-lipid, the dexamethasone and the lipophilic anti-cancer drug are formulated in the range of 1:1:0.75:0.1 to 1:1:0.75:0.5, and b) genetic material encoding a gene, the expression of which in tumor cells has an anti-tumor effect; wherein the genetic material is complexed with the cationic liposome in the range of 1:2 to 1:8 molar charge ratio, wherein the anti-cancer drug is ESC8 and wherein the cationic lipid comprises DODEAC (N, N-dihydroxyethyl, N, N-dioctadecyl ammonium chloride) and the neutral co-lipid comprises cholesterol.

13. The synergistic composition as claimed in claim 1, wherein the anti-cancer drug is nutilin.

* * * * *